(12) United States Patent
Zhang et al.

(10) Patent No.: US 11,029,316 B2
(45) Date of Patent: Jun. 8, 2021

(54) MULTIPLEX PROTEOME QUANTIFICATION METHOD BASED ON ISOBARIC DIMETHYL LABELING

(71) Applicant: DALIAN INSTITUTE OF CHEMICAL PHYSICS, CHINESE ACADEMY OF SCIENCES, Liaoning (CN)

(72) Inventors: Lihua Zhang, Liaoning (CN); Jianhui Liu, Liaoning (CN); Yuan Zhou, Liaoning (CN); Kaiguang Yang, Liaoning (CN); Yukui Zhang, Liaoning (CN)

(73) Assignee: DALIAN INSTITUTE OF CHEMICAL PHYSICS, CHINESE ACADEMY OF SCIENCES, Liaoning (CN)

(*) Notice: Subject to any disclaimer, the term of this patent is extended or adjusted under 35 U.S.C. 154(b) by 658 days.

(21) Appl. No.: 15/754,212

(22) PCT Filed: Nov. 20, 2015

(86) PCT No.: PCT/CN2015/095077
§ 371 (c)(1),
(2) Date: Feb. 21, 2018

(87) PCT Pub. No.: WO2017/031843
PCT Pub. Date: Mar. 2, 2017

(65) Prior Publication Data
US 2018/0246117 A1    Aug. 30, 2018

(30) Foreign Application Priority Data
Aug. 26, 2015   (CN) .......................... 201510532694.8

(51) Int. Cl.
    *G01N 33/68*    (2006.01)
    *G01N 30/04*    (2006.01)
    (Continued)

(52) U.S. Cl.
    CPC ......... *G01N 33/6848* (2013.01); *G01N 30/02* (2013.01); *G01N 30/04* (2013.01);
    (Continued)

(58) Field of Classification Search
    CPC ........ G01N 30/02; G01N 30/04; G01N 30/06; G01N 30/72; G01N 30/7233;
    (Continued)

(56) References Cited

U.S. PATENT DOCUMENTS

2008/0199848 A1    8/2008   Bode-Boger et al.

FOREIGN PATENT DOCUMENTS

CN    103884574 A    6/2014
CN    104076098 A    10/2014
(Continued)

OTHER PUBLICATIONS

Tamar Geiger et al., "Use of stable isotope labeling by amino acids in cell culture as a spike-in standard in quantitative proteomics", Nature Protocols, vol. 6, No. 2, 2011, pp. 147-157.
(Continued)

*Primary Examiner* — Jeremy C Flinders
(74) *Attorney, Agent, or Firm* — Novick, Kim & Lee, PLLC; Allen Xue

(57) ABSTRACT

A multiplex proteome quantification method based on isobaric dimethyl labeling implements dimethyl labeling of peptide N-terminal in an acidic condition and C-terminal in an alkaline condition one after another by means of Hall the property that a dimethylation reaction has different rates on an amino group at the peptide N-terminal and an amino group on a Lysine side chain at the peptide C-terminal in the (Continued)

acidic condition. Multiplex labeling of peptide samples is implemented by means of the organic combination of various isotope forms of a dimethyl labeling reagents. The mass-to-charge ratios in MS1 of peptides after multiplex labeling are completely the same, the mass-to-charge ratios of the fragment ions in MS2 are different, and multiplex quantitative analyses are carried out by extracting the intensity values of corresponding fragment ions in the MS2.

9 Claims, 3 Drawing Sheets

(51) Int. Cl.
  *G01N 30/06* (2006.01)
  *G01N 30/02* (2006.01)
  *G01N 30/72* (2006.01)
(52) U.S. Cl.
  CPC .............. *G01N 30/06* (2013.01); *G01N 30/72* (2013.01); *G01N 33/6827* (2013.01); *G01N 30/7233* (2013.01); *G01N 2458/15* (2013.01); *G01N 2570/00* (2013.01)
(58) Field of Classification Search
  CPC ........... G01N 33/6827; G01N 33/6848; G01N 2458/15; G01N 2570/00
  See application file for complete search history.

(56) References Cited

FOREIGN PATENT DOCUMENTS

| CN | 104237363 A | 12/2014 |
| GB | 0811298 | 7/2008 |
| WO | 2009153577 A1 | 12/2009 |

OTHER PUBLICATIONS

Fangjun Wang et al., "A six-plex proteome quantification strategy reveals the dynamics of protein turnover", Scientific Reports, vol. 3, No. 1827, pp. 1-6.

Yue Wu et al., "Five-plex isotope dimethyl labeling for quantitative proteomics", Chem Commun, Feb. 2014, vol. 50, No. 14, pp. 1708-1710.

Leila Choe et al., "8-Plex quantitation of changes in cerebrospinal fluid protein expression in subjects undergoing intravenous immunoglobulin treatment for Alzheimer's disease", Proteomics, 2007, vol. 7, pp. 3651-3660.

Loyc Dayon et al., "Relative Quantification of Proteins in Human Cerebrospinal Fluids by MS/MS Using 6-Plex Isobaric Tags", Analytical Chemistry, 2008, vol. 80, No. 8, pp. 2921-2931.

Christian J. Koehler et al., "An Approach for Triplex-Isobaric Peptide Termini Labeling (Triplex-IPTL)", Analytical Chemistry, 2013, vol. 85, pp. 2478-2485.

Yuan Zhou et al., "Mass Defect-Based Pseudo-Isobaric Dimethyl Labeling for Proteome Quantification", Analytical Chemistry, 2013, vol. 85, No. 22, pp. 10658-10663.

Paul J Boersema et al. "Multiplex peptide stable isotope dimethyl labeling for quantitative proteomics", Nature Protocols, 2009, vol. 4, No. 4, pp. 484-494.

MULTIPLEX PROTEOME QUANTIFICATION METHOD BASED ON ISOBARIC DIMETHYL LABELING

FIELD OF THE INVENTION

The present invention relates to a multiplex isobaric labeling quantification method, which can implement simultaneous quantitation of up to six protein samples. The method has advantages of high labeling efficiency and selectivity, high quantitative accuracy and precision, high quantitative coverage, wide dynamic range and high-throughput of quantitative analysis of the proteome, and can be used for quantitative proteome analysis of large biological samples and dynamic processes of organisms.

BACKGROUND OF THE INVENTION

Changes of protein content can reflect life processes and reveal the state of the diseases. Studying these changes can provide basic data support for finding drug targets and potential disease markers. Facing the large number of proteome samples and the changes of contents thereof with time and space, quantitative methods that enable the simultaneous analysis of multiplex proteome samples are urgently needed on the premise of quantitative accuracy, precision and dynamic range.

At present, the multiplex proteome quantification method usually uses a stable isotope labeling strategy based on LC-MS. There are two kind of methods according to the position from which the quantitative information is derived in mass spectrometry data: a MS1-based quantitative method; and a MS2-based quantitative method. The MS1-based quantitative method is implemented by comparing peak intensities or areas of multiplex labeled samples in MS1 scan. At present, there are methods such as SILAC triple labeling (Nat. Protoc. 2011, 6, 147.), sextuple labeling method which combines SILAC with dimethyl labeling (Scientific Reports 2013, 3, 1827.), and dimethyl quintuple labeling (Chem. Commun. 2014, 50, 1708.). However, these methods bear the shortage of low signal-to-noise ratio, low sensitivity, data analysis difficulties and increased complexity of MS1 spectrum.

Compared to the above methods, MS2-based quantification method reduces the complexity of MS1 spectrum due to the same mass-to-charge ratio of MS1 of multiple labeling, which can be conducive to deep quantitative coverage; and the signal-to-noise ratio of MS2 is significantly improved, which is conducive to improving the quantitative accuracy and dynamic range. In the MS2-based quantitative method, the reporter ions-based quantitative method can achieve iTRAQ octuplet labeling (Proteomics, 2007, 7, 3651.) and TMT sextuple labeling (Anal Chem, 2008, 80, 2921.). But the method affects quantitative accuracy owing to the co-isolated interference. Recently, more and more attention has been paid on the fragment ion-based quantitative methods. There are methods such as IPTL triple labeling (Anal. Chem. 2013, 85, 2478.) and mass defect-based quadruple labeling (Anal. Chem. 2013, 85, 10658.). These methods have advantages of high quantitative accuracy, good precision and wider dynamic range, but the throughput is still not enough.

SUMMARY OF THE INVENTION

The present invention develops a multiplex proteome quantification method based on isobaric dimethyl labeling. By combining the thinking of IPTL with the mass defect-based labeling method, the dimethyl labeling is carried out on the peptide N-terminal and C-terminal of Lys-C digests under different pH conditions, to achieve isobaricly sextuple labeling and quantification by the fragment ions in an MS2.

To achieve the above purpose, the technical scheme adopted in the present invention is:

1. Protein samples are denatured, reduced, alkylated and then incubated overnight by adding a Lys-C protease according at a certain enzyme/protein ratio.

2. According to a property that a reaction has different rates on an amino group at a peptide N-terminal and an amino group on a Lysine side chain at a peptide C-terminal in an acidic condition, the dimethyl labeling is first selectively carried out on the amino group at the peptide N-terminal of a protein digests in the acidic condition; and then correspondingly carried out on the amino group on the Lysine side chain at the peptide C-terminal in an alkaline condition; the pH value of the acidic condition is controlled to be 2.0 to 5.0, and the labeling time is 5 to 120 min; and the pH value of the alkaline condition is controlled to be 7.5 to 12, and the labeling time is 5 to 120 min.

3. The above steps are repeated for the labeling of two, three, four, five and six samples.

4. Among the multiplex labeling methods above, the sextuple labeling reagents are:

Peptide N-terminal: $^{13}CH_2O+NaBH_3CN$-Peptide C-terminal: $CD_2O+NaBD_3CN$;

Peptide N-terminal: $CD_2O+NaBH_3CN$-Peptide C-terminal: $^{13}CH_2O+NaBD_3CN$;

Peptide N-terminal: $^{13}CD_2O+NaBH_3CN$-Peptide C-terminal: $CH_2O+NaBD_3CN$;

Peptide N-terminal: $CH_2O+NaBD_3CN$-Peptide C-terminal: $^{13}CD_2O+NaBH_3CN$;

Peptide N-terminal: $^{13}CH_2O+NaBD_3CN$-Peptide C-terminal: $CD_2O+NaBH_3CN$;

Peptide N-terminal: $CD_2O+NaBD_3CN$-Peptide C-terminal: $^{13}CH_2O+NaBH_3CN$;

5. The multiplex labeled samples are mixed, and then analyzed by LC-MS. The mass spectrometry comprises Orbitrap, TOF and FT-ICR.

6. The obtained MS1 of the collected peptides in the MS has the same mass-to-charge ratio, and each fragment ion in an MS2 has difference in mass-to-charge ratio. As the multiplex labeling simultaneously shown on each MS2, the intensity values of the fragment ions of a, b and y which are simultaneously shown in the sextuple labeling of each labeled peptide on the MS2 are extracted and summed as an intensity of the labeled peptide. The multiplex quantitative analysis methods based on the fragment ion intensity in the MS2 are implemented by comparing the intensity of each of the sextuple labeling as the relative quantitative results.

The advantages of the present invention are as follows:

1. The labeling efficiency and selectivity are high: Using the optimized labeling conditions, the labeling efficiency and selectivity of the peptide thereof are above 95%. Besides, the labeling reagents are cost-effective.

2. The same number of atoms of isotopes is introduced among multiplex labeling, which avoids the differences of retention time of multiplex peptides at the reversed-phase chromatography due to the introduction of different numbers of deuterium atoms.

3. The throughput of quantitative analysis is high, which can simultaneously analyze six samples, thereby greatly saving the analysis time of the samples and improving the quantitative accuracy.

4. The labeling method introduces a labeling idea of the mass defect, which effectively reduces the complexity of MS2 spectrum, thereby being benefit for the identification of the MS2.

5. The quantitative coverage, accuracy and precision are high.

6. The quantitative dynamic range is wide.

DETAILED DESCRIPTION OF THE EMBODIMENTS

Embodiment 1

1. Protein Digestion

Figure 1:
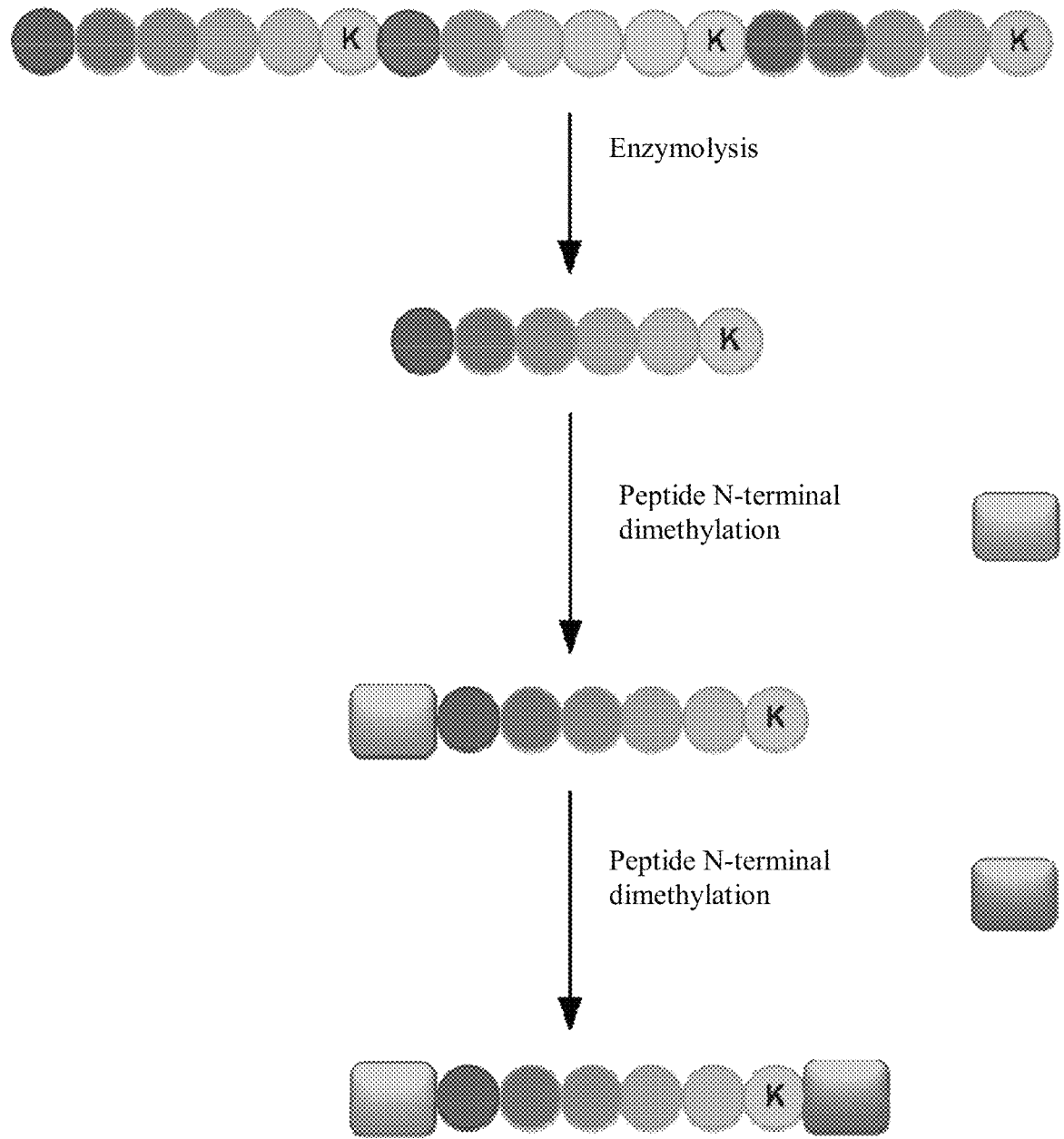
FIG. 1 is a schematic diagram of isobaric dimethyl labeling.
Figure 2:
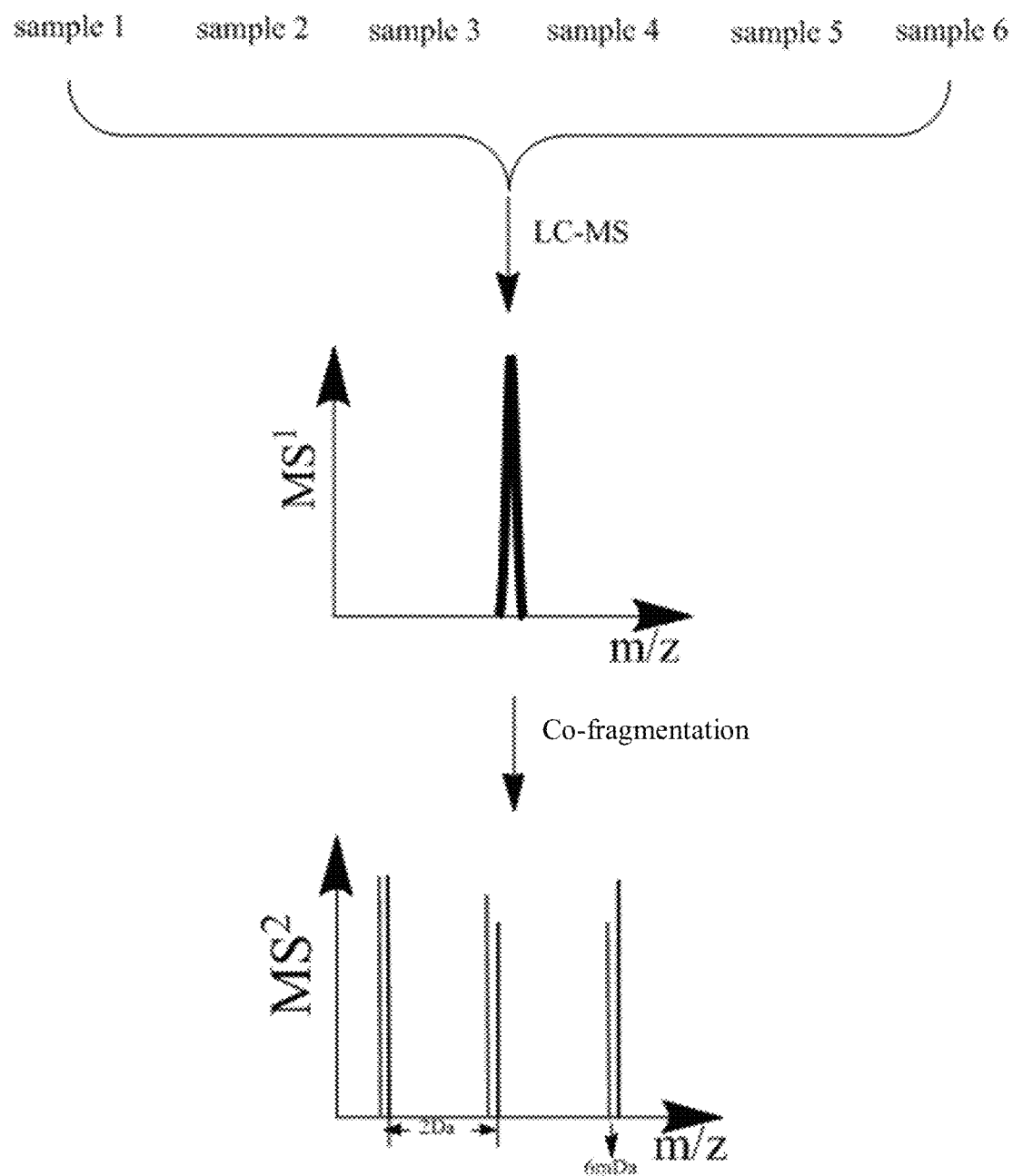
FIG. 2 is a theory mass spectrum diagram of the mixture of the labeling of six samples.

The protein samples are dissolved in 8 M urea solution, and the DTT is added to reach the final concentration of 10 mM, then the samples are denatured and reduced at 56° C. for 1 h, and the IAA is added to reach the final concentration of 20 mM, and the samples are kept in the dark at room temperature for 30 min, and then the urea solution is then diluted to 1 M. Finally, the Lys-C is added to the samples in a ratio of 1:50 (enzyme/protein, w/w), and the samples are digested at 37° C. overnight. The samples are desalted by C18 trap column and lyophilized, and then resolved with water.

2. Dimethyl Labeling of Peptides

The sextuple dimethyl labeling is separately carried out on the peptides. As shown in Table 3, the specific labeling methods are as follows:

The first labeling: The peptide digests are loaded on a C18-trap column and firstly balanced by 1.5% (v/v) $CH_3COOH$ aqueous solution of the acid solution. The dimethyl labeling is selectively carried out on an amino group at peptide N-terminal in the acid solution, and the labeling solution is obtained by adding 50 μL of 4% (v/v) $^{13}CH_2O$ and 50 μL of 0.6 M (w/v) $NaBH_3CN$ to 1 mL 1.5% (v/v) $CH_3COOH$ aqueous solution for 20 min with the flow rate of 50 μL/min. The trap column is then washed with 1.5% (v/v) $CH_3COOH$ aqueous solution of the acid solution and water, and then is balanced by the phosphate buffer with pH value of 8.0 of the alkaline solution. The dimethyl labeling is carried out on an amino group on a Lysine side chain at peptide C-terminal in the alkaline condition, and the labeling solution is obtained by adding 50 μL of 4% (v/v) $CD_2O$ and 50 μL of 0.6 M (w/v) $NaBD_3CN$ to 1 mL phosphate buffer with pH value of 8.0 for 10 min with the flow rate of 50 μL/min. Finally, the trap column is washed with the phosphate buffer solution with pH value of 8.0 of the alkaline solution and water in sequence; and finally the sample is eluted with 80% (v/v) ACN from the trap column.

The second labeling: The labeling method is the same as the first labeling. The labeling solution in an acidic condition is changed to the solution obtained by adding 50 μL of 4% (v/v) $CD_2O$ and 50 μL of 0.6 M (w/v) $NaBH_3CN$ to 1 mL 1.5% (v/v) $CH_3COOH$ aqueous solution. The labeling solution in an alkaline condition is changed to the solution obtained by adding 50 μL of 4% $^{13}CH_2O$ and 50 μL of 0.6 M (w/v) $NaBD_3CN$ to 1 mL phosphate buffer solution with pH value of 8.0.

The third labeling: The labeling method is the same as the first labeling. The labeling solution in an acidic condition is changed to the solution obtained by adding 50 μL of 4% (v/v)$^{13}CD_2O$ and 50 μL of 0.6 M (w/v) $NaBH_3CN$ to 1 mL 1.5% (v/v) $CH_3COOH$ aqueous solution. The labeling solution in an alkaline condition is changed to the solution obtained by adding 50 μL of 4% (v/v) $CH_2O$ and 50 μL of 0.6 M (w/v) $NaBD_3CN$ to 1 mL phosphate buffer solution with pH value of 8.0.

The fourth labeling: The labeling method is the same as the first labeling. The peptide digests are loaded on a C18-trap column and firstly balanced by 1.5% (v/v) $CH_3COOH$ $D_2O$ solution of the acid solution. The dimethyl labeling is selectively carried out on an amino group at peptide N-terminal in the acid solution, and the labeling solution is obtained by adding 50 μL of 4% (v/v) $CH_2O$ and 50 μL of 0.6 M (w/v) $NaBD_3CN$ to 1 mL 1.5% (v/v) $CH_3COOH$ $D_2O$ solution for 30 min with the flow rate of 25 μL/min. The trap column is then washed with 1.5% $CH_3COOH$ aqueous solution of the acid solution and water in sequence, and then is balanced by the phosphate buffer solution with pH value of 8.0 of the alkaline solution. The dimethyl labeling is carried out on an amino group on a Lysine side chain at peptide C-terminal in the alkaline condition, and the labeling solution is obtained by adding 50 μL of 4% (v/v)$^{13}CD_2O$ and 50 μL of 0.6 M (w/v) $NaBH_3CN$ to 1 mL phosphate buffer solution with pH value of 8.0 for 10 min with the flow rate of 50 μL/min. Finally, the trap column is washed with the phosphate buffer solution with pH value of 8.0 of the alkaline solution and water in sequence; and finally the sample is eluted with 80% (v/v) ACN from the trap column.

The fifth labeling: The labeling method is the same as the fourth labeling. The labeling solution in an acidic condition is changed to the solution obtained by adding 50 μL of 4% (v/v)$^{13}CH_2O$ and 50 μL of 0.6 M (w/v) $NaBD_3CN$ to 1 mL 1.5% (v/v) $CH_3COOH$ $D_2O$ solution. The labeling solution in an alkaline condition is changed to the solution obtained by adding 50 μL of 4% (v/v) $CD_2O$ and 50 μL of 0.6 M (w/v) $NaBH_3CN$ to 1 mL phosphate buffer solution with pH value of 8.0.

The sixth labeling: The labeling method is the same as the fourth labeling. The labeling solution in an acidic condition is changed to the solution obtained by adding 50 μL of 4% (v/v) $CD_2O$ and 50 μL of 0.6 M (w/v) $NaBD_3CN$ to 1 mL 1.5% (v/v) $CH_3COOH$ $D_2O$ solution. The labeling solution in an alkaline condition is changed to the solution obtained by adding 50 μL of 4% (v/v)$^{13}CH_2O$ and 50 μL of 0.6 M (w/v) $NaBH_3CN$ to 1 mL phosphate buffer solution with pH value of 8.0.

All the samples are lyophilized and then resolved to the mass concentration of 0.5 mg/mL with buffer solution A (containing aqueous solution of 2% (v/v) ACN and 0.1% (v/v) FA). The samples are mixed with fixed ratios to be for MS analysis.

3. LC-MS Analysis.

Liquid chromatography condition: Mobile phases are buffer solution A (containing aqueous solution of 2% (v/v) ACN and 0.1% (v/v) FA) and buffer solution B (containing aqueous solution of 98% (v/v) water and 0.1% (v/v) FA). The gradient separation is performed using buffer solution B with a gradient of 0% for 10 min, the linear gradient separation is performed using buffer solution B with a gradient of 5% to 25% for 125 min, and then the linear gradient separation is performed using buffer solution B with a gradient of 25% to 35% for 10 min at a flow rate of 300 nL/min.

Mass acquisition condition: A Q-Exactive MS is used, and a data-dependent acquisition (DDA) mode is used. The resolution of Full MS is 70000 (m/z=200), and the mass range is from 350 to 1800 m/z. Ten most intensive ions are selected for MS/MS fragmentation. The dynamic exclusion time is 20 s. The activation type is HCD, a normalized collision energy is 28%, a isolation window is 2.0 Da, fixed first mass of the MS2 is 50.0 Da, and the resolution of MS/MS is 35000 (m/z=200). Each sample above is injected in parallel for three times.

4. Data Analysis

The acquired raw files by MS use a MaxQuant (v1.2.2.5) software package, and use Andromeda as database search engine, to conduct database search. The fixed modification is set as cysteine carbamidomethylation; and the variable modification is set as acetyl (Protein N-term), oxidation (M), N-term and K respectively select the corresponding dimethyl labeling modifications. The human protein database is downloaded from ftp.uniprot.org on July, 2013. The mass tolerance of the MS1 is 6 ppm, and the mass tolerance of the MS2 is 20 ppm. The protease is Lys-C. Two missed cleavage sites are allowed. The FDRs less than 0.01 for proteins and peptides are required. For quantitative analysis, the identified peptides are theoretically fragmented and matched with the corresponding mgf files to extract all the eligible fragment ions. Then the ion pairs are matched, the appeared ion of each sample is kept, and then most of all the fragment ion intensities of the labeling are summed as the ion intensity of the peptide. The ion intensities of multiplex labeled peptides are compared in pairs as relative quantitative ratios of identified peptides of the spectra. The median of the spectra matching the same peptide is taken as a quantitative result of the peptide, and the medians of all identified peptides for the same protein are taken as a quantitative result of the protein. All the results of three replicates are combined, and the values of the same protein are averaged as the final quantitative result of the protein. All the analyses are completed by SPSS (v20) and Excel (v2010).

Figure 3:
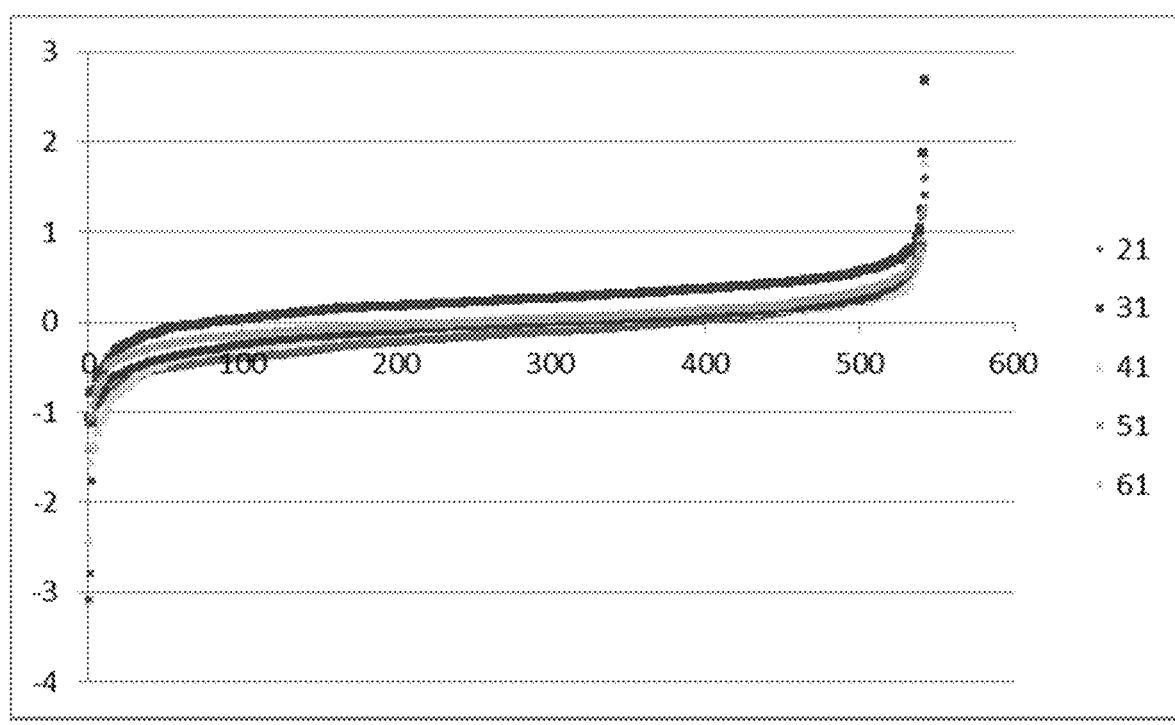
FIG. 3 is a diagram of equivalently mixed quantitative results of six samples. The figure shows results obtained by taking the log 2 for the quantitative ratio after the six samples are mixed in a ratio of 1:1:1:1:1:1.

Method Evaluation:

1. Six samples are mixed in a ratio of 1:1:1:1:1:1. The quantitative coverage is more than 95%. The simultaneous quantitative analysis of six protein samples can be implemented. The quantitative accuracy and precision results are shown in Table 1 and FIG. 3. The quantitative results are close to the theoretical values with high precision.

2. Wide quantitative dynamic range: The samples are mixed in a ratio of 1:2:5:10:20:50. The results are shown in Table 2. This method can achieve dynamic ranges of 50-fold with good quantitative accuracy, and doesn't have underestimated effect based on a reporter ion quantitative method, which is due to the fact that the method is based on a quantitative method of multiple fragment ions of the MS2, thereby effectively reducing the quantitative interference of the co-eluted peptides.

Embodiment 2

The labeling process is carried out in a centrifuge tube. After the labeling in an acidic condition, the solvent is exchanged by a C18-trap column. Then the labeling in an alkaline condition is carried out after elution. The other processes are the same as those in Embodiment 1.

Embodiment 3

The labeling process in the acidic condition is carried out in a centrifuge tube. After the solvent is exchanged by the C18-trap column, the labeling in the alkaline condition is carried out on the trap column. The other processes are the same as those in Embodiment 1.

Embodiment 4

The dimethyl labeling is selectively carried out on the amino group at the peptide N-terminal in the acidic condition, and the labeling solution comprises 1% (v/v) $CH_3COOH$ aqueous solution, 4% (v/v) $CH_2O$ aqueous solution and isotopic forms thereof, and 0.6 M (w/v) $NaBH_3CN$ solution and isotopic forms thereof. The labeling time is 10 min. The other processes are the same as those in Embodiment 1.

Embodiment 5

The quadruple labeling is achieved by using the first four labeling methods in Embodiment 1. The other processes are the same as those in Embodiment 1.

TABLE 1

Quantitative accuracy and precision results of six equivalently mixed samples

|  | 30H/30L | 32L/30L | 32H/30L | 34L/30L | 34H/30L |
|---|---|---|---|---|---|
| Average | 0.92 | 1.20 | 0.96 | 0.98 | 1.03 |
| RSD/% | 14 | 16 | 14 | 14 | 14 |

TABLE 2

Quantitative results of dynamic range

| | Theoretical ratio (Heavy/Light Labeling) | | | | |
|---|---|---|---|---|---|
| | 2 | 5 | 10 | 20 | 50 |
| Experimental ratio (Heavy/Light Labeling) | 2.54 | 5.34 | 13.28 | 21.39 | 53.00 |

TABLE 3

Sextuple labeling methods

| Multi-plicities | Abbrev-iation | Labeling reagent of N-terminal | Flow rate and time for labeling of N-terminal | Labeling reagent of K-terminal | Flow rate and time for labeling of K-terminal | Mass increase of both terminals (N-terminal-K-terminal/Da) |
|---|---|---|---|---|---|---|
| 1 | 2L-6H | $^{13}CH_2O$ + $NaBH_3CN$ | 20 min 50 µL/min | $CD_2O$ + $NaBD_3CN$ | 10 min 50 µL/min | 30.03801-34.06896 |

TABLE 3-continued

Sextuple labeling methods

| Multi-plicities | Abbrev-iation | Labeling reagent of N-terminal | Flow rate and time for labeling of N-terminal | Labeling reagent of K-terminal | Flow rate and time for labeling of K-terminal | Mass increase of both terminals (N-terminal-K-terminal/Da) |
|---|---|---|---|---|---|---|
| 2 | 4H-4L | $CD_2O$ + $NaBH_3CN$ | | $^{13}CH_2O$ + $NaBD_3CN$ | | 32.05641-32.05056 |
| 3 | 6L-2H | $^{13}CD_2O$ + $NaBH_3CN$ | | $CH_2O$ + $NaBD_3CN$ | | 34.06312-30.04385 |
| 4 | 2H-6L | $CH_2O$ + $NaBD_3CN$ | 30 min 25 µL/min | $^{13}CD_2O$ + $NaBH_3CN$ | | 30.04385-34.06312 |
| 5 | 4L-4H | $^{13}CH_2O$ + $NaBD_3CN$ | | $CD_2O$ + $NaBH_3CN$ | | 32.05056-32.05641 |
| 6 | 6H-2L | $CD_2O$ + $NaBD_3CN$ | | $^{13}CH_2O$ + $NaBH_3CN$ | | 34.06896-30.03801 |

The method has advantages of high accuracy, good precision, and wide dynamic range, which can simultaneously implement the simultaneous quantitative analysis of six protein samples, thereby greatly improving the throughput of the quantitative analysis of proteins and saving the analysis time.

We claim:

1. A multiplex proteome quantification method, comprising:
   digesting a protein into a plurality of peptides using a protease that cleaves at a carboxyl side of lysine; and
   performing dimethyl labeling of a peptide among the plurality of peptides to produce a plurality of labeled peptides, wherein the dimethyl labeling comprises:
   performing a first dimethyl labeling to a peptide N-terminal under a first acidic condition using a first dimethyl labeling reagent and the second dimethyl labeling to a peptide C-terminal on a Lysine side chain under a first alkaline condition using a second dimethyl labeling reagent to form a first labeled peptide;
   performing a third dimethyl labeling to a peptide N-terminal under a second acidic condition using a third dimethyl labeling reagent and a fourth dimethyl labeling to a peptide C-terminal on a Lysine side chain under a second alkaline condition using a fourth dimethyl labeling reagent to form a second labeled peptide;
   performing a fifth dimethyl labeling to a peptide N-terminal under a third acidic condition using a fifth dimethyl labeling reagent and a sixth dimethyl labeling to a peptide C-terminal on a Lysine side chain under a third alkaline condition using a sixth dimethyl labeling reagent to form a third labeled peptide,
   wherein each of the first dimethyl labeling reagent, the second dimethyl labeling reagent, the third dimethyl labeling reagent, the fourth dimethyl labeling reagent, the fifth dimethyl labeling reagent, and the sixth dimethyl labeling reagent comprises a first compound selected from $CH_2O$, $^{13}CH_2O$, $CD_2O$, and $^{13}CD_2O$, and a second compound selected from $NaBH_3CN$ and $NaBD_3CN$, and
   the plurality of labeled peptides have a same mass-to-charge ratio;
   ionizing the plurality of labeled peptides and acquiring ionized forms of the plurality of labeled peptides in MS1 of a mass spectrometer;
   separating and fragmenting the ionized forms of the plurality of labeled peptides and acquiring fragment ions in MS2 of the mass spectrometer; and
   performing multiplex quantitative analysis based on intensities of the fragment ions in the MS2.

2. The method according to claim 1, wherein the plurality of labeled peptides further comprises a fourth labeled peptide, or the fourth labeled peptide and a fifth labeled peptide, or the fourth labeled peptide, the fifth labeled peptide, and a sixed labeled peptide,
   wherein the first to the sixth dimethyl labeling reagents are selected from a reagent comprising $^{13}CH_2O$ and $NaBH_3CN$, a reagent comprising $CD_2O$ and $NaBD_3CN$, a reagent comprising $CD_2O$ and $NaBH_3CN$, a reagent comprising $^{13}CH_2O$ and $NaBD_3CN$, a reagent comprising $^{13}CD_2O$ and $NaBH_3CN$, a reagent comprising $CH_2O$ and $NaBD_3CN$, a reagent comprising $CH_2O$ and $NaBH_3CN$, a reagent comprising $^{13}CD_2O$ and $NaBD_3CN$, a reagent comprising $^{13}CH_2O$ and $NaBH_3CN$, a reagent comprising $CD_2O$ and $NaBD_3CN$, a reagent comprising $CD_2O$ and $NaBH_3CN$, and a reagent comprising $^{13}CH_2O$ and $NaBH_3CN$.

3. The analysis method according to claim 2, comprising displaying a spectrum of each of the plurality of labeled peptides on a same spectrum of MS2;
   extracting and summing up intensity values of fragment ions of a, b and y for each of the plurality of labeled peptides on the MS2;
   assigning the sum of intensity values of fragment ions of a, b and y as an intensity of the corresponding labeled peptide; and comparing the intensity of each of the plurality of labeled peptides.

4. The method according to claim 2, wherein the protein is denatured, reduced, alkylated and then is incubated by the protease.

5. The method according to claim 1, wherein the mass spectrometer comprises an Orbitrap analyzer, or a TOF analyzer, or an FT-ICR analyzer.

6. The method according to claim 1, wherein the protease is a Lys-C protease.

7. The method according to claim 1, performing a first dimethyl labeling proceeds the second dimethyl labeling.

8. The method according to claim 1, wherein, in each of the first acidic condition, the second acidic condition, and the third acidic condition, a pH value is 2.0 to 5.0 and a labeling time is 5 to 120 min.

9. The method according to claim 1, wherein, in each of the first alkaline condition, the second alkaline condition, and the third alkaline condition, a pH value is 7.5 to 12 and a labeling time is 5 to 120 min.

* * * * *